(12) United States Patent
Labischinski et al.

(10) Patent No.: US 7,795,207 B2
(45) Date of Patent: Sep. 14, 2010

(54) LIPOPEPTIDE COMPOSITIONS

(76) Inventors: Harald Labischinski, c/o Combinature Biopharm AG, Robert-Rössle-Strasse 10, Berlin (DE) D-13125; Stefan Pelzer, c/o Combinature Biopharm AG, Robert-Rössle-Strasse 10, Berlin (DE) D-13125; Horst Priefert, c/o Combinature Biopharm AG, Robert-Rössle-Strasse 10, Berlin (DE) D-13125; Andreas Vente, c/o Combinature Biopharm AG, Robert-Rössle-Strasse 10, Berlin (DE) D-13125; Sven-Eric Wohlert, c/o Combinature Biopharm AG, Robert-Rössle-Strasse 10, Berlin (DE) D-13125

( * ) Notice: Subject to any disclaimer, the term of this patent is extended or adjusted under 35 U.S.C. 154(b) by 191 days.

(21) Appl. No.: 11/604,010

(22) Filed: Nov. 21, 2006

(65) Prior Publication Data

US 2007/0219124 A1 Sep. 20, 2007

Related U.S. Application Data

(60) Provisional application No. 60/740,094, filed on Nov. 28, 2005.

(30) Foreign Application Priority Data

Nov. 21, 2005 (DE) .................... 10 2005 056 194

(51) Int. Cl.
*A61K 38/14* (2006.01)

(52) U.S. Cl. .................... 514/2; 514/8; 514/10
(58) Field of Classification Search .................... None
See application file for complete search history.

(56) References Cited

U.S. PATENT DOCUMENTS 5,629,288 A 5/1997 Lattrell et al.
6,624,143 B1 9/2003 Vertesy et al.

FOREIGN PATENT DOCUMENTS

| DE | 19807972 | 2/1998 |
|---|---|---|
| EP | 0688789 | 3/1995 |
| WO | WO01/82971 | 11/2001 |
| WO | WO 01/82971 | * 11/2001 |
| WO | WO 01/97851 | * 12/2001 |
| WO | WO01/97851 | 12/2001 |
| WO | WO 02/32459 | * 4/2002 |
| WO | WO02/32459 | 4/2002 |

OTHER PUBLICATIONS

Irie et al. (1983) J. Pharm, Dyn., 6, 408-414, "Protective Mechanism of β-cyclodextrin for the hemolysis induced with phenothiazine neuroleptics *in vitro*".
Uekama et al. (1998) Chem. Rev., 98, 2045-2076, "Cyclodextrin drug carrier systems".

* cited by examiner

*Primary Examiner*—Christopher R. Tate
*Assistant Examiner*—Roy Teller
(74) *Attorney, Agent, or Firm*—Swanson & Bratschun, L.L.C.

(57) ABSTRACT

The invention relates to a pharmaceutical composition comprising as an active agent a lipopeptide in a physiologically effective dose and a cyclodextrin or a cyclodextrin derivative.

14 Claims, No Drawings

LIPOPEPTIDE COMPOSITIONS

FIELD OF THE INVENTION

The invention relates to new pharmaceutical compositions containing lipopeptides, to the use of such compositions, to methods for the production thereof and to the use thereof as drugs.

BACKGROUND OF THE INVENTION AND PRIOR ART

Secondary metabolites, which are produced by living organisms, in particular microorganisms, and the chemical variants derived therefrom are successfully used as active agents in medicine. Particularly for the control of infectious diseases, the use of secondary metabolites has proven effective. A large portion of the antibiotics used today were isolated from bacteria in the soil, the so-called actinomycetes. Due to the development of resistances against the respectively used drugs, there is a permanent demand of new antibiotic active agents with novel activity mechanisms. In spite of their excellent antibiotic and other pharmacological properties, for many secondary metabolites the use as a drug is at last unsuccessful because of the in most cases also very distinct toxic properties for man.

Antibiotics from the class of the lipopeptides, which are characterized by a linear or cyclic peptide portion or a combination of both, with naturally and/or non-naturally derivatized and/or non-derivatized amino acids, with which a saturated or unsaturated acyl residue is connected, which optionally may be interrupted by one or several phenyl or cycloalkyl groups or connected with such groups or interrupted by one or several oxygen or nitrogen atoms, have been found in the past as very effective against fungi and Gram-positive bacteria. For the majority of these compounds, however, toxic properties are also known.

The compound daptomycin belonging to the class of the A-21978C lipopeptides for instance damages the skeletal muscle (Oleson et al. 2000, Anti-microbial agents and chemotherapy, Vol. 44 No 11; 2948-2953), and a series of further lipopeptides, for instance lichenysin (Grangemard I. et al., Applied Biochemistry and Biotechnology, Volume 90, Number 3, 2001, pp. 199-210(12)), surfactin A (Hanka Symmank, Peter Franke, Wolfram Saenger and Frank Bernhard, Modification of biologically active peptides: production of a novel lipohexapeptide after engineering of *Bacillus subtilis* surfactin synthetase) FR131535 and echinocandin (Fujie A, Iwamoto T, Sato B, Muramatsu H, Kasahara C, Furuta T, Hori Y, Hino M, Hashimoto S., Bioorg Med Chem Lett. 2001 Feb. 12; 11(3):399-402. FR131535, a novel water-soluble-echinocandin-like lipopeptide: synthesis and biological properties), Fengycin (J. of Antibiotics 29 (1986) 888-901), iturin A (Aranda F J, Teruel J A, Ortiz A., Biochem Biophys Acta. 2005 Jul. 15; 1713(1):51-6. Further aspects on the hemolytic activity of the antibiotic lipopeptide iturin A), and lipopeptides (DE 19807972) similar to amphomycin and friulimicin act in a hemolytic manner.

An essential problem for the application of these lipopeptides as drugs is however the elimination of the toxicological properties without impairing the antibiotic activity of the substances. For the application of these substances as drugs, it is therefore necessary to find pharmaceutical compositions, which compared to the pure substance have improved pharmacological properties. It is known, for instance, that the hemolytic properties of a substance or of an ion are reduced in the presence of the serum albumin, and this is caused by the interaction with the serum albumin ("masking effect") (Caffrey J M Jr, Smith H A, Schmitz J C, Merchant A, Frieden E.: Hemolysis of rabbit erythrocytes in the presence of copper ions. Inhibition by albumin and ceruloplasmin. Biol Trace Elem Res. 1990 Apr. 25; (1):11-9). This masking effect with the serum albumin causes however in many cases also the loss of the desired properties of molecules, and thus also of the antibiotic activity of lipopeptides as illustrated in example 1 of this invention.

It is known in the art to use cyclodextrins in pharmaceutical compositions. Due to their circular structure, cyclodextrins have a hydrophilic exterior and hydrophobic inner pocket. By enclosing in particular hydrophobic sections of the molecules, cyclodextrins can achieve a "molecular encapsulation" or "masking" of active agents, which are used for instance as a protective envelope of sensitive molecules in cosmetic and pharmaceutical formulations. Thereby, improved solubilities of substances, but also reduced toxicities, such as for instance a reduction of the hemolytic properties of molecules (J. Pharmacobiodyn. 1983 6(6): 408-14. Protective mechanism of beta cyclodextrin for the hemolysis induced with phenothiazine neuroleptics in vitro. Irie T, Sunada M, Otagiri M, Uekama K.) are obtained.

TECHNICAL OBJECT OF THE INVENTION

It is therefore the technical object of the invention to provide new pharmaceutical compositions with antibacterially, antivirally and/or antimycotically acting lipopeptides, the tolerance of which is improved while maintaining the physioclogical effectiveness such that even with very high concentrations, which will for example occur during infusions for short times at the place of application, only little toxic side effects will be encountered.

BASICS OF THE INVENTION AND EMBODIMENTS

For achieving this technical object, the invention teaches a pharmaceutical composition comprising as an active agent an antibacterially, antivirally, and/or antimycotically acting lipopeptide in a physiologically effective dose and a physiologically tolerated cyclodextrin or a cyclodextrin derivative.

The invention is based on the surprising finding that specially by using cyclodextrins or cyclodextrin derivatives not only a reduction of the hemolytic properties of antibiotically acting lipopeptides is achieved, but that rather at the same time the antibiotic effect of the lipopeptides is maintained, whereas on the other hand for instance a masking with HSA will lead to a reduced or completely suppressed antibiotic effect.

The lipopeptide preferably has a structure according to formula I,

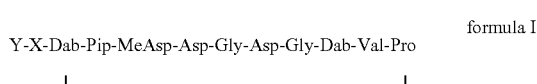

formula I wherein X=one of the amino acids Asn or Asp, wherein Y=a straight-chain or branched, saturated or unsaturated aliphatic acyl residue with 6 to 22 carbon atoms, which optionally is interrupted by one or several phenyl or cycloalkyl groups or connected with such groups or interrupted by one or several oxygen atoms. The amino acids of the peptide portion of the molecules may be derivatized (US 2005/0153876 A1). In the case that X=Asn, it is friulimicin or a friulimicin derivative. In the case that that X=Asp, it is amphomycin or an amphomycin derivative. Y may in particular be:

$(CH_3)_2CH(CH_2)_7CH=CHCH_2CO—$, $CH_3(CH_2)_6CO—$, $CH_3(CH_2)_7CO—$, $CH_3(CH_2)_8CO—$, $CH_3(CH_2)_9CO—$, $CH_3(CH_2)_{10}CO—$, $CH_3(CH_2)_{11}CO—$, $CH_3(CH_2)_{12}CO—$, $CH_3(CH_2)_{13}CO—$, $CH_3(CH_2)_{14}CO—$, $CH_3(CH_2)_{15}CO—$, $CH_3CH(CH_3)(CH_2)_8CO—$, $CH_3CH(CH_3)(CH_2)_9CO—$, $CH_3CH(CH_3)(CH_2)_{10}CO—$, $CH_3CH(CH_3)(CH_2)_{11}CO—$, $CH_3CH(CH_3)(CH_2)_{12}CO—$, $H_2C=CH(CH_2)_8CO—$, $H_2C=CH(CH_2)_9CO—$, $CH_3(CH_2)_7CH=CHCO—$ (trans), $CH_3(CH_2)_8CH=CHCO$-(trans), $CH_3(CH_2)_{12}CH=CHCO$-(trans), $CH_3(CH_2)_3CH=CH(CH_2)_7CO$-(cis), $CH_3(CH_2)_3CH=CH(CH_2)_7CO$-(trans), $CH_3(CH_2)_3CH=CH(CH_2)_8CO$-(trans), $CH_3(CH_2)_5CH=CH(CH_2)_7CO$-(cis), $CH_3(CH_2)_5CH=CH(CH_2)_7CO$-(trans), $CH_3(CH_2)_5CH=CH(CH_2)_8CO$-(cis), $CH_3(CH_2)_{10}CH=CH(CH_2)_4CO$-(cis), $CH_3(CH_2)_{10}CH=CH(CH_2)_4CO$-(trans), $CH_3(CH_2)_7CH=CH(CH_2)_7CO$-(cis), $CH_3(CH_2)_7CH=CH(CH_2)_7CO$-(trans), $CH_3(CH_2)_5CH=CH(CH_2)_9CO$-(trans), $CH_3(CH_2)_3(CH_2CH=CH)_2(CH_2)_7CO$-(cis), $CH_3(CH_2)_3(CH_2CH=CH)_2(CH_2)_2CO$-(trans), $CH_3(CH_2)_3(CH_2CH=CH)_2(CH_2)_9CO$-(cis), $CH_3(CH_2CH=CH)_3(CH_2)_7CO$-(cis), $CH_3(CH_2)_3(CH_2CH=CH)_3(CH_2)_4CO$-(cis), $CH_3(CH_2CH=CH)_4(CH_2)_4CO$-(cis), $CH_3(CH_2)_3(CH_2CH=CH)_4(CH_2)_3CO$-(cis), $CH_3(CH_2CH=CH)_6(CH_2)_2CO$-(cis), $H_2C=CH(CH_3)_8CO—$, $CH_3(CH_2)_3CH=CH(CH_2)_7CO—$, $CH_3(CH_2)_7CH=CH(CH_2)_7CO—$, $CH_3(CH_2)_4CH=CH—CH=CH—(CH_2)_8CO—$, $(CH_3)_2C=CHCH_2[CH_2C(CH_3)=CHCH_2]_2CO—$, Phe-Phe-CH_2CO—, Phe-$(CH_2)_9$CO—, Phe-O—$(CH_2)_{10}$CO—, $CH_3(CH_2)_7$-Phe-CO—, Phe-Phe-CO—, $CH_3(CH_2)_6$-Phe-CO—, $CH_3(CH_2)_6$—O-Phe-CO, $CH_3(CH_2)_7$—O-Phe-CO—, Phe-$(CH_2)_2$-Phe-CO—, $CH_3CH_2$-Phe-$(CH_2)_2$-Phe-CO—, Phe-Phe-$(CH_2)_2$-Phe-CO—, Phe-$(CH_2)_2$-Phe-$(CH_2)_2$-Phe-CO—, $CH_3(CH_2)_3$-Phe-$(CH_2)_2$-Phe-CO—, $CH_3(CH_2)_5$—O-Phe-$(CH_2)_2$-Phe-CO—, $(CH_3)_2CH(CH_2)_6CH=CHCH_2CO$-(cis), $(CH_3)_2CH(CH_2)_6CH=CHCH_2CO$-(trans), $(CH_3)_2CH(CH_2)_7CH=CHCH_2CO$-(cis) $(CH_3)_2CH(CH_2)_7CH=CHCH_2CO$-(trans), $CH_3CH_2(CHCH_3)(CH_2)_5CH=CHCH_2CO$-(cis), $CH_3CH_2(CHCH_3)(CH_2)_5CH=CHCH_2CO$-(trans), $CH_3CH_2(CHCH_3)(CH_2)_7CH=CHCH_2CO$-(cis), $CH_3CH_2(CHCH_3)(CH_2)_7CH=CHCH_2CO$-(trans), $CH_3CH_2(CHCH_3)(CH_2)_7CH=CHCH_2CO$-(cis), $CH_3(CH_2)_8CH=CHCO$-(cis), $CH_3(CH_2)_8CH=CHCO$-(trans), $CH_3(CH_2)_9CH=CHCO$-(cis), $CH_3(CH_2)_8CH=CHCO$-(trans), $CH_3(CH_2)_7CH=CHCO$-(cis), $CH_3(CH_2)_7CH=CHCO$-(trans), wherein Phe is a benzene ring being not substituted or substituted one time or two to four times by C1-8 alkyl, and wherein -Phe- is ortho, metha, or para bonding.

For producing such lipopeptides in detail, reference is made for instance to the documents DE 198 07 972 A1, EP 0 629 636 A1, EP 0 688 789 A1 and US 2005/0153876 A1.

The lipopeptide may be selected, independently from formula I, from the group comprising "amphomycin, amphomycin derivatives, friulimicin, friulimicin B, friulimicin derivatives, daptomycin, daptomycin derivatives, aspartocin, aspartocin derivatives, glumamycin, glumamycin derivatives, crystallomycin, crystallomycin derivatives, zaomycin, zaomycin derivatives, tsushimycin, tsushimyin derivatives, laspartomycin, laspartomycin derivatives, brevistin, brevistin derivatives, cerexin B, cerexin B derivatives, syringomycin and its derivatives, antibiotic A-30912 and its derivatives, antibiotic A-54145 and its derivatives and antibiotic A-21978C and its derivatives".

The lipopeptide may furthermore be selected, independently from formula I, from the group comprising "$C_{15}$-AMPHOMYCIN, $C_{15}$-AMPHOMYCIN-9-GLY, $C_{15}$-AMPHOMYCIN-9-GLY-LYS, $C_{15}$-AMPHOMYCIN-9-LEU, $C_{10}$-AMPHOMYCIN, $C_{11}$-AMPHOMYCIN, $C_{12}$-AMPHOMYCIN, $C_{13}$-AMPHOMYCIN, $C_{14}$-AMPHOMYCIN, $C_{16}$-AMPHOMYCIN, $C_{17}$-AMPHOMYCIN, $C_{18}$-AMPHOMYCIN, OLEOYL-AMPHOMYCIN, $CH_3—(CH_2)_{11}$—O—P—PH—C(=O)-AMPHOMYCIN, $CH_3—(CH_2)_{15}$—O—P—PH—C(=O)AMPHOMYCIN, HO—$(CH_2)_{15}$—C(=O)-AMPHOMYCIN, $CH_3—(CH_2)_9$-0-P—PH—C(=O)-AMPHOMYCIN, $CH_3—(CH_2)_7$-0-P—PH—C(=O)-AMPHOMYCIN, $CH_3(CH_2)_{11}$—NH-SUCCINYL-AMPHOMYCIN, $C_{12}$-P-HYDRAZINBENZOIC ACID-AMPHOMYCIN, $C_{15}$-AMPHOMYCIN-9-GABA, $C_{14}$-AMPHOMYCIN-9-GLY, $C_{15}$-AMPHOMYCIN-9-SAR, $C_{15}$-AMPHOMYCIN-9-AHX, $C_{15}$-AMPHOMYCIN-9-INA, $C_{15}$-AMPHOMYCIN-9-(P—N0_2—PHE), $C_{15}$-AMPHOMYCIN-9-GLY-PHE, $C_{15}$-AMPHOMYCIN-9-GLU, $C_{15}$-AMPHOMYCIN-9-(P—F—PHE), $C_{15}$-AMPHOMYCIN-9-(β-CHA), $C_{15}$-AMPHOMYCIN-9-HPHE, $C_{15}$-AMPHOMYCIN-9-GLY-GLY-GLY, $C_{15}$-AMPHOMYCIN-9-C(=0)-$(CH_2)_{10}$—NH_2, $C_{15}$-AMPHOMYCIN-9-(β-CYANO-ALA), $C_{15}$-AMPHOMYCIN-9-ILE, $C_{15}$-AMPHOMYCIN-9-GLY-VAL, $C_{15}$-AMPHOMYCIN-9-ASN, $C_{15}$-AMPHOMYCIN-9-TYR, $C_{15}$-AMPHOMYCIN-9-TRP, $C_{15}$-AMPHOMYCIN-9-PHG, $C_{15}$-AMPHOMYCIN-9-GLY-GLY, $C_{15}$-AMPHOMYCIN-9-GLN, $C_{15}$-AMPHOMYCIN-9-THR, $C_{15}$-AMPHOMYCIN-9-PRO-GLY, $C_{15}$-AMPHOMYCIN-9-GLY-LEU, $C_{15}$-AMPHOMYCIN-9-TYR (ET), $C_{15}$-AMPHOMYCIN-9-GLY-SUC, $C_{15}$-AMPHOMYCIN-9-GLY-AC, $C_{13}$-AMPHOMYCIN-9-GABA, $C_{14}$-AMPHOMYCIN-9-GLY-LYS, $C_{15}$-AMPHOMYCIN-9-TYR (ME), $C_{13}$-AMPHOMYCIN-9-GLY, $C_{13}$-AMPHOMYCIN-9-(β-ALA), $C_{13}$-AMPHOMYCIN-9-SAR, $C_{13}$-AMPHOMYCIN-9-AHX, $C_{12}$-AMPHOMYCIN-9-GABA, $C_{12}$-AMPHOMYCIN-9-GLY, $C_{14}$-AMPHOMYCIN-9-(β-ALA), $C_{14}$-AMPHOMYCIN-9-SAR, $C_{14}$-AMPHOMYCIN-9-AHX, $C_{14}$-AMPHOMYCIN-9-GABA, $C_{13}$-AMPHOMYCIN-9-ALA, $C_{13}$-AMPHOMYCIN-9-(D-ALA), $C_{13}$-AMPHOMYCIN-9-(D-PRO), $C_{15}$-AMPHOMYCIN-9-(D-ALA), $C_{15}$-AMPHOMYCIN-9-(D-PRO), $C_{15}$-AMPHOMYCIN-9-GLY-GABA, $C_{15}$-AMPHOMYCIN-9-GLY-(D-ALA), $C_{15}$-AMPHOMYCIN-9-(β-ALA)-AHX, $C_{15}$-AMPHOMYCIN-9-GABA-VAL, $C_{15}$-AMPHOMYCIN-9-GABA-AHX, $C_{12}$-AMPHOMYCIN-9-(β-ALA), $C_{12}$-AMPHOMYCIN-9-SAR, $C_{16}$-AMPHOMYCIN-9-SAR, $C_{10}$-AMPHOMYCIN-9-(β-ALA), $C_{10}$-AMPHOMYCIN-9-SAR, $C_{17}$-AMPHOMYCIN-9-SAR, $C_{16}$-AMPHOMYCIN-9-(β-ALA), $C_{17}$-AMPHOMYCIN-9-(β-ALA), $C_{15}$-AMPHOMYCIN-9-GLY-$C_6$, $C_{15}$-AMPHOMYCIN-9-ALA, $CH_3—(CH_2)_{15}$—NH—C(=0)-AMPHOMYCIN-9-GLY, $CH_3—(CH_2)_{15}$—SO_2-AMPHOMYCIN-9-GLY, $C_2$-PABA-AMPHOMYCIN, $C_{12}$-(P-APA)-AMPHOMYCIN-9-GLY, $C_{12}$-PABA-AMPHOMYCIN-9-GLY, $CH_3$-$(CH_2)_{11}$—O—P—PH—C(=0)-AMPHOMYCIN-9-GLY, $C_{12}$-(P-TRANS-CINNAMYL)-AMPHOMYCIN-9-GLY, $CH_3—(CH_2)_{11}$—O—P—PH—C)-GLY-AMPHOMYCIN-9-GLY, $C_{14}$-PABA-GLY-AMPHOMYCIN-9-GLY, $CH_3(CH_2)_{11}$—NH—C(=0)-AMPHOMYCIN-9-GLY, $C_{15}$-AMPHOMYCIN-9-AHX-GLY, $C_{15}$-AMPHOMYCIN-9-GABA-GABA, $C_{15}$-AMPHOMYCIN-9-HPRO, $C_{15}$-AMPHOMYCIN-9-(D-PIP), $CH_3—(CH_2)_{11}$—NH—C(=0)-AMPHOMYCIN-9-(β-ALA), $CH_3—(CH_2)_{11}$—NH—C(=0)-AMPHOMYCIN-9-SAR, $CH_3—(CH_2)_{15}$—SO_2-GLY-AMPHOMYCIN, $CH_3—(CH_2)_9$—SO_2-PHE-AMPHOMYCIN, $CH_3—(CH_2)_9$—SO_2-GLY- AMPHOMYCIN-9-LYS, $CH_3-(CH_2)_9-SO_2$-GLY-AMPHOMYCIN-9-GLY, $C_{12}$-GLY-AMPHOMYCIN, $C_8$-(P-APA)-AMPHOMYCIN, $C_{14}$-GLY-AMPHOMYCIN, $C_{16}$-GLY-AMPHOMYCIN, $C_{18}$-GLY-AMPHOMYCIN, $C_{12}$-(P-AMINOPHENYLPROPANOYL)-AMPHOMYCIN, $C_{12}$-(P-AMINOPHENYLPROPANOYL)-2-AMPHOMYCIN, $CH_3-(CH_2)_9-O-P-PH-C(=O)$-GLY-AMPHOMYCIN, $C_{12}$-(M-APA)-AMPHOMYCIN, $C_{15}$-[ASP-(OTBU)]-AMPHOMYCIN, $C_{10}$-(M-APA)-AMPHOMYCIN, $CH_3-(CH_2)_7-(CH_3-(CH_2)_5)$ $CH-C(=O)$-GLY-AMPHOMYCIN, $C_{15}$-PHG-AMPHOMYCIN, $C_{15}$-(D-PHE)-AMPHOMYCIN, $PH-O-(CH_2)_{11}$-GLY-AMPHOMYCIN, $C_{10}$-(L-BBTA)-AMPHOMYCIN, $C_{12}$-(P-APA)-AMPHOMYCIN, $C_{12}$-(P-AMINO-TRANS-CINNAMYL)-AMPHOMYCIN, $CH_3-(CH_2)_{11}-O-P-PH-C(=O)$-GLY-AMPHOMYCIN, $CH_3-(CH_2)_9$-(P-APA)-AMPHOMYCIN, $C_{12}$-PABA-GLY-AMPHOMYCIN, $C_{15}$-AMPHOMYCIN-9-(D-ORN), $C_{14}$-AMPHOMYCIN-9-GLY-LYS, $C_{14}$-AMPHOMYCIN-9-LYS, $C_{14}$-AMPHOMYCIN-9-ORN, $C_{13}$-AMPHOMYCIN-9-GLY-LYS, $C_{15}$-AMPHOMYCIN-9-LYS, $C_{15}$-AMPHOMYCIN-9-ORN, $C_{15}$-AMPHOMYCIN-9-GDAB, $C_{15}$-AMPHOMYCIN-9-DAP, $C_{13}$-AMPHOMYCIN-9-LYS, $C_{13}$-AMPHOMYCIN-9-ORN, $C_{13}$-AMPHOMYCIN-9-GDAB, $C_{13}$-AMPHOMYCIN-9-DAP, $C_{12}$-AMPHOMYCIN-9-LYS, $C_{12}$-AMPHOMYCIN-9-GDAB, $C_{14}$-AMPHOMYCIN-9-GDAB, C14-AMPHOMYCIN-9-DAP, $C_{16}$-AMPHOMYCIN-9-GLY-LYS, $C_{17}$-AMPHOMYCIN-9-GLY-LYS, $C_{12}$-AMPHOMYCIN-9-GLY-LYS, $C_{15}$-AMPHOMYCIN-9-SAR-ORN, $C_{15}$-AMPHOMYCIN-9-SAR-GDAB, $C_{15}$-AMPHOMYCIN-9-SAR-DAP, $C_{15}$-AMPHOMYCIN-9-(β-ALA), $C_{15}$-AMPHOMYCIN-9-(β-ALA)-ORN, β-ISOMER OF $C_{15}$-AMPHOMYCIN-9-(β-ALA), ANHYDROISOMER OF $C_{15}$-AMPHOMYCIN-9-(β-ALA), $C_{15}$-AMPHOMYCIN-9-(D-PRO)-(D-LYS), $C_{15}$-AMPHOMYCIN-9-GLY-(D-LYS), $C_{15}$-AMPHOMYCIN-9-GLY-ORN, $C_{15}$-AMPHOMYCIN-9-GLY-GDAB, $C_{15}$-AMPHOMYCIN-9-(β-ALA)-LYS, $C_{15}$-AMPHOMYCIN-9-GABA-LYS, $C_{15}$-AMPHOMYCIN-9-GLY-DAP, $C_{15}$-AMPHOMYCIN-9-GLY-HLYS, $C_{15}$-AMPHOMYCIN-9-GABA-GDAB, $C_{15}$-AMPHOMYCIN-9-PRO, $C_{15}$-AMPHOMYCIN-9-AIB, $C_{15}$-AMPHOMYCIN-9-MECYS, $C_{15}$-AMPHOMYCIN-9-NVL, $C_{15}$-AMPHOMYCIN-9-ABU, $C_{15}$-AMPHOMYCIN-9-CIT, $C_{15}$-AMPHOMYCIN-9-$(ME)_2$ARG, $C_{15}$-AMPHOMYCIN-9-HYP, $C_{15}$-AMPHOMYCIN-9-(P-APA), $C_{15}$-AMPHOMYCIN-9-VAL, $C_{15}$-AMPHOMYCIN-9-$(ME)_3$LYS, $C_{15}$-AMPHOMYCIN-9-NLE, $C_{15}$-AMPHOMYCIN-9-LYS, $C_{15}$-AMPHOMYCIN-9-(β-ALA)-(5-AVA), $C_{15}$-AMPHOMYCIN-9-(β-ALA)-VAL, β-ISOMER OF $C_{15}$-AMPHOMYCIN-9-(β-ALA)-VAL, $C_{15}$-AMPHOMYCIN-9-(S-AVA)-(β-ALA), $C_{15}$-AMPHOMYCIN-9-GLY-LYS-GLY, $C_{15}$-AMPHOMYCIN-9-GLY-LYS-LYS, $C_{15}$-AMPHOMYCIN-9-GLY-GLY-LYS, $C_{15}$-AMPHOMYCIN-9-LYS-GLY, $C_{15}$-AMPHOMYCIN-9-LYS-LYS, $C_{15}$-AMPHOMYCIN-9-LYS-LYS-LYS, $C_{15}$-AMPHOMYCIN-9-GLY-(D-LEU), $C_{15}$-AMPHOMYCIN-9-GLY-AHX, $C_{15}$-AMPHOMYCIN-9-SAR-AHX, $C_{15}$-AMPHOMYCIN-9-SAR-LYS, $C_{15}$-AMPHOMYCIN-9-DAP-(β-N-(β-ALA)), $C_{15}$-AMPHOMYCIN-9-$C_6$, $C_{15}$-AMPHOMYCIN-9-PLA, $C_{15}$-AMPHOMYCIN-9-PCA, $C_{15}$-AMPHOMYCIN-9-(CARBAMOYL-LEU), $C_{15}$-AMPHOMYCIN-9-$C_8$, $C_{15}$-AMPHOMYCIN-9-CHEXYL, $C_{15}$-AMPHOMYCIN-9-$C_4$, $C_{15}$-AMPHOMYCIN-9-(2-NORBORNANEACETYL), $C_{15}$-AMPHOMYCIN-9-(N-BENZOYL-TYR-PABA), $C_{15}$-AMPHOMYCIN-9-((S)-(+)-5-OXO-2-TETRAHYDROFURANCARBONYL), $C_{15}$-AMPHOMYCIN-9-PHENYLPROPYNYL, $C_{15}$-AMPHOMYCIN-9-(CARBAMOYL-β-ALA), $C_{15}$-AMPHOMYCIN-9-ACRYL, $C_{15}$-AMPHOMYCIN-9-(1-NAPTHYLACETYL), $C_{15}$-AMPHOMYCIN-9-(4-PHENOXYBENZOYL), $C_{15}$-AMPHOMYCIN-9-(2-NAPTHYLACETYL), $C_{15}$-AMPHOMYCIN-9-(2-FURYL), $C_{15}$-AMPHOMYCIN-9-CROTONYL, $C_{15}$-AMPHOMYCIN-9-(3,4-(METHYLENEDIOXY)PHENYLACETYL), $C_{15}$-AMPHOMYCIN-9-$C_{10}$, $C_{15}$-AMPHOMYCIN-9-(γ-OXO-5-ACENAPTHENE-BUTANYL), $C_{15}$-AMPHOMYCIN-9-HYDROCINNAMYL, $C_{15}$-AMPHOMYCIN-9(α-KETOBUTYL), $C_{15}$-AMPHOMYCIN-9-GERANYL, $C_{15}$-AMPHOMYCIN-9-(O-ANISYL), $C_{15}$-AMPHOMYCIN-9-PHENYLECATYL, $C_{15}$-AMPHOMYCIN-9(2-BUTYNYL), $C_{15}$-AMPHOMYCIN-9-(3,5-BIS($CF_3$)PHENYLACETYL), $C_{15}$-AMPHOMYCIN-9-(3,4-METHYLENEDIOXY-CINNAMYL), $C_{15}$-AMPHOMYCIN-9-(TRANS-CINNAMYL), $C_{15}$-AMPHOMYCIN-9-ACETOXYACETYL, $C_{15}$-AMPHOMYCIN-9-(1-ADAMANTANYLCARBONYL), $C_{15}$-AMPHOMYCIN-9-(4-COTININECARBONYL), $C_{15}$-AMPHOMYCIN-9-(4-FLUOROBENZOLYL), $C_{15}$-AMPHOMYCIN-9-(S-ACETYLTHIOGLYCOYL), $C_{15}$-AMPHOMYCIN-9-(4-BUTOXYBENZOYL), $C_{15}$-AMPHOMYCIN-9-(6-OXOHEPTANOYL), $C_{15}$-AMPHOMYCIN-9-OLEATE, $C_{15}$-AMPHOMYCIN-9-(4-PENYLBENZOYL), $C_{15}$-AMPHOMYCIN-9-(3-PHENOXYBENZOYL), $C_{15}$-AMPHOMYCIN-9-(C(=O)-$(CH_2)_2$-PIPERIDINE, $C_{15}$-AMPHOMYCIN-9(N,N'-DIMETHYL-GABA), $C_{15}$-AMPHOMYCIN-9-(N-ETHYL-GLY), $C_{15}$-AMPHOMYCIN-9-SAR-(N,N-DIMETHYL-GLY), $C_{15}$-AMPHOMYCIN-9-(N-BENZYL-GLY), $C_{15}$-AMPHOMYCIN-9-(N,N-DIETHYL-β-ALA), $C_{10}$-AMPHOMYCIN-9-$C_{10}$, $C_{15}$-AMPHOMYCIN-9-(N-METHYL-GABA), $CH_3-(CH_2)_{15}-NH-C(=O)$-AMPHOMYCIN, $C_{15}$-AMPHOMYCIN-9-PGLU, $CH_3(CH_2)_{11}-NH-C(=O)$-AMPHOMYCIN, $CH_3-(CH_2)_7-NH-C(=O)$-AMPHOMYCIN, $CH_3-(CH_2)_{13}-NH-C(=O)$-AMPHOMYCIN, $CH_3-(CH_2)_{11}-NH-C(=O)$-AMPHOMYCIN, $C_{15}$-AMPHOMYCIN-C(=O)-NH-N-BUTYL, $-C_{15}$-AMPHOMYCIN-C(=O)-NH-CYCLOHEXYL, $C_{15}$-AMPHOMYCIN-C(=O)-NH-FURFURYL, $C_{15}$-AMPHOMYCIN-C(=O)-NH-2-FLUOROBENZYL, $C_{15}$-AMPHOMYCINC(=O)-NH-M-$CF_3$-PHENYL, $C_{15}$-AMPHOMYCIN-C(=O)-NH-P-$CF_3$-PHENYL, $C_{15}$-AMPHOMYCIN-C(=O)-NH-3-FLUOROPHENYL, $C_{15}$-AMPHOMYCIN-(D-SER), $C_{15}$-AMPHOMYCIN-(D-TYR), $C_{15}$-AMPHOMYCIN-(D-TRP), $C_{13}$-AMPHOMYCIN-9-GLU, $C_{15}$-AMPHOMYCIN-9-(4-HYDROXYBENZYL), $C_{15}$-AMPHOMYCIN-9-N,N-DI-(P-HYDROXYBENZYL), $C_{15}$-AMPHOMYCIN-9(N,N-DIMETHYLGLYCINE), $CH_3-(CH_2)_9-SO_2$-GLY-AMPHOMYCIN, $CH_3-(CH_2)_{15}-SO_2$-PHE-AMPHOMYCIN, $CH_3-(CH_2)_{13}-NH-C(=O)$-AMPHOMYCIN-9-GLY-LYS, $CH_3-(CH_2)_{13}-NH-C(=O)$-AMPHOMYCIN-9-(β-ALA), $CH_3-(CH_2)_{13}-NH-C(=O)$-AMPHOMYCIN-9-GLY, $C_{12}$-PABA-AMPHOMYCIN-9-(β-ALA), $C_{16}$-(P-APA)-AMPHOMYCIN, $C_8$-PABA-AMPHOMYCIN, $C_{10}$-PABA-AMPHOMYCIN, C11-PABA-AMPHOMYCIN, $C_{13}$-PABA-AMPHOMYCIN, $CH_3-(CH_2)_{10}-NH-C(=O)$-(β-ALA)-AMPHOMYCIN, $CH_3-(CH_2)_{15}-NH-C(=O)$-(P-PHENYLACETYL)AMPHOMYCIN, $CH_3-(CH_2)_7-NH-C(=O)$-(P-PHENYLACETYL)AMPHOMYCIN, $CH_3-(CH_2)_{13}-NH-C(=O)$-(P-PHENYLACETYL)AMPHOMYCIN, $CH_3-(CH_2)_{10}-NH-C(=O)$-(P-PHENYLACETYL)AMPHOMYCIN, CH₃—(CH₂)₁₃—NH—C(=O)-(GABA)-AMPHOMYCIN, CH₃—(CH₂)₁₃—NH—C(=O)-(M-PHENYLACETYL)-AMPHOMYCIN, C₁₀-(M-AMINOBENZOYL)-AMPHOMYCIN, C₁₁-(M-AMINOBENZOYL)-AMPHOMYCIN, CH₃—(CH₂)₁₃—NH—C(=O)-(β-ALA)-AMPHOMYCIN, C₁₂-(M-AMINOBENZOYL)-AMPHOMYCIN, C₁₃-(M-AMINOBENZOYL)-AMPHOMYCIN, BORONAT-PINACOL-ESTER-RESIN, 4'-OCTYL-BIPHENYL-4-CARBOXYL-AMPHOMYCIN, C₁₃-(P-APA)AMPHOMYCIN, C₁₄-(β-APA)-AMPHOMYCIN, CH₃—(CH₂)₁₅—NH—C(=O)-(M-PHENYLACETYL)-AMPHOMYCIN, C₁₄-(M-APA)-AMPHOMYCIN, C₁₃-(P-APA)-AMPHOMYCIN, CH₃-(CH₂)₁₀—NH—C(=O)-GABA-AMPHOMYCIN, N,N'-DI-C₈-(M,M-DIAMINOBENZOYL)-AMPHOMYCIN, CH₃—(CH₂)₇—NH—C(=O)-(M-PHENYLACETYL)-AMPHOMYCIN, CH₃—(CH₂)₁₃—NH—C(=O)-GLY-AMPHOMYCIN, 1-DODECYL-1H-(1,2,3)-TRIAZOLE-4-CARBOXYLIC ACID, 1-DODECYL-1H-(1,2,3)-TRIAZOLE-4-CARBOXYL-AMPHOMYCIN, C₁₅-(M-APA)-AMPHOMYCIN, C₁₃-(ASP-(OME))-AMPHOMYCIN, C₁₅-(PAPA)-AMPHOMYCIN, C₁₅-(ASP-(OME))-AMPHOMYCIN, C11-(ASP-(OTBU))-AMPHOMYCIN, C₁₃-(ASP-(OTBU))-AMPHOMYCIN, C₁₁-(ASP-(OME))-AMPHOMYCIN, C₁₅-ASP-(OME))-AMPHOMYCIN, C₁₅-AMPHOMYCIN-9-C(=O)—NH—(O—CF₃—PHENYL), N,N'-DI-C₆-(M,MDIAMINOBENZOYL)-AMPHOMYCIN, N,N'-DI-C₁₂-(M,MDIAMINOBENZOYL)-AMPHOMYCIN, CH₃—(CH₂)₇—NH—C(=O)-(β-ALA)-AMPHOMYCIN, (4-PHENYL-BENZOYL)-AMPHOMYCIN, (2-PHENYLMETHYL)-BENZOYL-AMPHOMYCIN, N,N-DIETHYL-PABA-AMPHOMYCIN, (3,4,5-TRIMETHOXYBENZOYL)-AMPHOMYCIN, (4-TBUTYLBENZOYL)-AMPHOMYCIN, (3-(PHENOXY)-BENZOYL)-AMPHOMYCIN, C₁₅-AMPHOMYCIN-9-(D-DAP), β-ISOMER OF CH₃—(CH₂)₁₃—NH—C(=O)-AMPHOMYCIN, β-ISOMER OF CH₃—(CH₂)₁₀—NH—C(=O)-(GABA)-AMPHOMYCIN, LYS-GLY-AMPHOMYCIN-9-C₁₅, LYS-GLY-AMPHOMYCIN-9-C₁₃, (ll-(PHENOXY)UNDECANOYL)-AMPHOMYCIN, N—C₁₂-((lS,4S)-4-AMINOCYCLOHEXYLCARBOXYLIC ACID), C₁₂-((lS,4S)-4-AMINOCYCLOHEXYLCARBOXYL)-AMPHOMYCIN, (2-DODECANOYLAMINO-THIAZOL-4-YL)-ACETIC ACID, (2-DODECANOYLAMINO-THIAZOL-4-YL) ACETYL-AMPHOMYCIN, 8-DODECYLOXY-QUINOLINE-2-CARBOXYLIC ACID, (8-DODECYLOXY-QUINOLINE-2-CARBONYL)-AMPHOMYCIN, β-ISOMER OF (8-DODECYLOXY-QUINOLINE-2-CARBONYL)-AMPHOMYCIN, C₁₅-AMPHOMYCIN-9-PHE, C₁₅-AMPHOMYCIN-9-C₁₅, C₁₅-AMPHOMYCIN-9-([2-(2-METHOXY-ETHOXY)-ETHOXY]-ACETYL), C₁₀-SAR-AMPHOMYCIN, C₁₄-SAR-AMPHOMYCIN, C₈-SAR-AMPHOMYCIN, C₁₅-AMPHOMYCIN-9-C12, C₁₅-AMPHOMYCIN-9-(11-PHENOXYUNDE-CANOYL), C₁₅-AMPHOMYCIN-9-(3FURAN-2-YL-ACRYLOYL), C₁₅-AMPHOMYCIN-9-(3(BENZENESULPHONYL)PROPIONOYL), C₁₅-AMPHOMYCIN-9-(4-(PYREN-2-YL)BUTYROYL), C₁₅-AMPHOMYCIN-9-SUC, C₁₅-AMPHOMYCIN-9-PROLYS, BOC-AMPHOMYCIN, AMPHOMYCIN-9-(β-ALA), AMPHOMYCIN-9-SAR, GLY-AMPHOMYCIN-9-FMOC, C₆-GLY-AMPHOMYCIN-9-FMOC, C₈-GLY-AMPHOMYCIN-9-FMOC, C₁₀-GLY-AMPHOMYCIN-9-FMOC, C8-(M-APA)-AMPHOMYCIN, CH₃—(CH₂)₁₀—NH—C(=O)-(M-PHENYLACETYL)-AMPHOMYCIN, 1-ADAMANTANE-(=O)-AMPHOMYCIN, (10-METHYL-UNDEC-2-ENOYL)-AMPHOMYCIN, (10-METHYL-DODEC-2-ENOYL)-AMPHOMYCIN, (12-METHYL-TETRADEC-2-ENOYL)-ASPARTOCIN, (10-METHYL-DODEC-2-ENOYL)-AMPHOMYCIN-9-GLY, (10-METHYL-DODEC-2-ENOYL)-AMPHOMYCIN-9-SAR, (10-METHYL-DODEC-2-ENOYL)-AMPHOMYCIN-9(β-ALA), (12-METHYL-TETRADEC-2-ENOYL)-ASPARTOCIN-9-GLY, (12-METHYL-TETRADEC-2-ENOYL)-ASPARTOCIN-9-SAR, (12-METHYL-TETRADEC-2-ENOYL)-ASPARTOCIN-9-(β-ALA), (12-ACETYLAMINODODECANOYL)-AMPHOMYCIN, and (12-AMINODODECOYL)-AMPHOMYCIN". With regard to the structure, the terminology thereof and the synthesis of such lipopeptides, reference is made to the document US 2005/0153876 A1, "Compositions of Lipopeptide Antibiotic Derivatives and Methods of Use thereof" of Migenix Inc., Canada. The above are lipopeptides, which are covered by formula Ia,

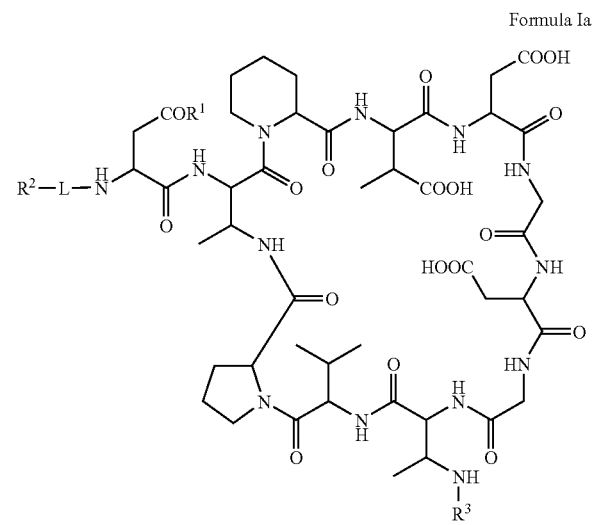

Formula Ia wherein in formula Ia R3 may also be bound by a residue L, wherein R1 is OH or NH₂, wherein L is at least one amino acid, at least one substituted amino acid, —R'—(CO)—, —R'—(CO)—(NR')—, or —O—Ph—(CO)—, wherein R' is respectively independently from each other identical or different, and a residue such as R3 or R5 can be defined, and/or wherein L—when R3 is bound by a residue L is identical or different and respectively independent from each other at least one amino acid, at least one substituted amino acid, —(CO)—, —R'—(CO)—, —SO₂—, —(CS)—, —(PO)—, —O-(PO)—, —O—(CO)—R'—O—(CO)(NR')—, —NH—(CO)—, —NR'—(CO)—, —R'—(CO)—, —R'—(CO)—(NR')—, or —O—Ph—(CO)—, wherein R' is respectively independently from each other identical or different and a residue such as R3 or R5 can be defined, wherein L for Dab9 is preferably —(CO)—, wherein R2 is —OR5, —SR5, NR5R5, —(CO)—R5, —(CO)—O—R5, —(CO)NHR4, —(CO)—NR4R4, —(CS)—NHR4, —(CS)—NR4R4, —(CNR4)-NHR4 or —(CNR4)-NR4R4, R5-(CO), S0₂R5, —(SO)—R5, —(PO)(OR5)₂, —(PO)(OR5), COOH, S0₃H, —P0₃H, —F, —Cl, —Br, —I, or trihalomethyl, wherein R3 is —H, —OR5, —SR5, —NR5R5, —CN, —NO₂, —N₃, —(CO)—R5, —(CO)—O—R5, —(CO)—NR5R5, —(CS)—NR5R5, —(CNR5)-NR5R5, —(CO)—H, —R5-(CO), —S0₂R5, —(PO)(OR5)₂, —(PO)(OR5), —CO₂H, —SO₃H, —PO₃H, —F, —Cl, —Br, —I, trihalomethyl, C1-C25 alkyl, substituted C1-C25 alkyl, C1-C25 heteroalkyl, substituted C1-C25 heteroalkyl, C5-C10 aryl, C5-C15 arylaryl, substituted C5-C15 arylaryl, C5-C15 biaryl, substituted C5-C15 biaryl, 5-10-membered heteroaryl, substituted 5-10-membered heteroaryl, C6-C26 arylalkyl, substituted C6-C26 arylalkyl, 6-26-membered heteroarylalkyl, substituted 6-26-membered heteroarylalkyl, at least one amino acid, or at least one substituted amino acid, wherein R4 is independently from each other identical or different C7-C10 alkyl, C17-C26 arylalkyl, 17-26-membered heteroarylalkyl, straight-chain or branched, saturated or singly or multiply unsaturated C7-C25 alkyl, optionally hydroxy-substituted, primary or secondary amine, at least one amino acid or at least one substituted amino acid, wherein R5 is independently from each other identical or different C1-C10 alkyl, C5-C10 aryl, 5-10-membered heteroaryl, C6-C26 arylalkyl, 6-26-membered heteroarylalkyl, straight-chain or branched, saturated or singly or multiply unsaturated C5-C25 alkyl, optionally hydroxy-substituted, primary or secondary amine, at least one amino acid or at least one substituted amino acid, or any combination thereof. In the case of an amino acid, R3 may be glycine, β-alanine, GABA, 5-aminopentanoic acid, 6-aminohexanoic acid, gDAB, Orn, Dap, hLys, sarcosine, lysine, glycine-lysine, or sarcosine-lysine. L may in particular be glycine, sarcosine, phenylglycine, phenylalanine, o-methylaspartic acid, o-t-butyl aspartic acid, pamonophenylacetyl, (p-aminophenylpropanoyl)ₙ with n=1 or 2, m-aminophenylacetyl, (m-aminophenylpropanoyl)ₙ with n=1 or 2, o-aminophenylacetyl, (o-aminophenylpropanoyl)ₙ with n=1 or 2, GABA, p-aminobenzoic acid (PABA), m-aminobenzoic acid, o-aminobenzoic acid, p-hydrazinobenzoic acid, m-hydrazinobenzoic acid, o-hydrazinobenzoic acid, p-amino-trans-cinnamyl, m-amino-trans-cinnamyl, O-amino-trans-cinnamyl, p-aminophenylacetic acid, m-aminophenylacetic acid, L-BBTA, or any combination thereof.

It is possible that the pharmaceutical composition includes several different lipopeptides in a physiologically effective dose each. Then it is a combination preparation or a wide band preparation.

In detail, the lipopeptide may be present in a free form or as an alkali or alkaline earth salt, preferably as a Na or Ca salt, in particular as a di-Ca salt (Ca₂Cl₂ salt), or as an ammonium salt.

The lipopeptide is added in the pharmaceutical composition preferably in a total amount (referred to the amount of all employed lipopeptides) from 0.01 to 80 wt. %, in particular from 0.05 to 50 wt. %, preferably from 0.1 to 30 wt. %, wherein the amount figures are referred to the completed composition.

In principle, all physiologically tolerated cyclodextrins and cyclodextrin derivatives can be employed. Cyclodextrins are cyclic oligosaccharides, which are composed of alpha-1,4-linked glucose components. Usually, six to eight glucose components (α, β, or γ-cyclodextrin) are connected with each other in a cyclodextrin molecule. Besides the naturally occurring, unmodified cyclodextrins, there is a large number of chemically modified cyclodextrin derivatives, which are physiologically tolerated and can be used for the purpose of the invention. The cyclodextrin or cyclodextrin derivative preferably is an α or β-cyclodextrin and may in particular have the general formula II,

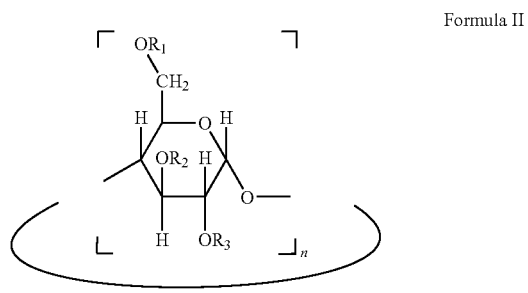

Formula II wherein R1, R2, and R3 may be identical or different and an arbitrary physiologically tolerated residue, preferably —H, C1-C8 alkyl, —SO₂OH, —PO(OH)₂, or —CO—R4 with R4=C1-C8 alkyl, wherein the C1-C8 alkyl may be single or multiple at identical or at different C atoms with —OH, —COOH, —CONHR5, —NHCOR6, —SO₂OH, —PO(OH)₂, or tetrazol-5-yl with R5=—H or C1-C4 alkyl and R6=carboxyl-phenyl, wherein n=6, 7 or 8, wherein R1, R2 and R3 may be randomized in different glucopyranose units, wherein an oxygen atom or several oxygen atoms of the glucopyranose units, in particular the oxygen atom at C6, may be substituted by sulfur atoms, including physiologically tolerated salts of such cyclodextrins. Preferably, the glucopyranose units are α-D or α-L-glucopyranose units. C1-C8 alkyl comprises in particular methyl, ethyl, propyl, isopropyl, butyl, isobutyl and tertiary butyl. On average, 1 to 3, preferably 1 to 2 of the residues R1, R2 and R3 may be different from H. Preferably, in particular R1 is different from —H. 1, 2, 3, 4, 5, 6, or if applicable 7 of the residues R1 of a cyclodextrin molecule may be different from —H. R2 and R3 may then be —H. In addition, however, 1, 2, 3, 4, 5, 6, or if applicable 7 of the residues R3 of a cyclodextrin molecule may also be different from —H.

In detail, the cyclodextrin or cyclodextrin derivative may be selected from the group consisting of "α-cyclodextrin, β-cyclodextrin, hydroxy(C1-C8 alkyl)-α-cyclodextrin, hydroxy-(C1-C8 alkyl)-β-cyclodextrin, (2-hydroxypropyl)-β-cyclodextrin, (2-hydroxypropyl)-α-cyclodextrin, sulfo-(C1-C8 alkyl)-ether-α-cyclodextrin, sulfo-(C1-C8 alkyl)-ether-β-cyclodextrin, sulfobutylether-α-cyclodextrin, sulfobutylether-β-cyclodextrin". For the derivatives, in particular the residue at the oxygen atom of the C6 atom is different from —H.

The cyclodextrin or cyclodextrin derivative may be present in the pharmaceutical composition in an amount from 0.01 to 99 wt. %, in particular from 0.05 to 80 wt. %, preferably 0.1 to 50 wt. %, referred to the completed composition.

Preferably, the lipopeptide in the pharmaceutical composition is mixed with the cyclodextrin or cyclodextrin derivative in a molar ratio lipopeptide/cyclodextrin from 100:1 to 1:500, preferably 10:1 to 1:50, most preferably 2:1 to 1:10, optionally under addition of additional and/or auxiliary substances in galenically common additions.

Usually, the pharmaceutical composition will comprise further additional and/or auxiliary substances, in particular galenic auxiliary substances, the selection of which depends from the selected form of administration. The galenic preparation of the pharmaceutical composition according to the invention may be made in a way being usual for this technology. As counter ions for ionic compounds may for instance be used Ca++, CaCl+, Na+, K+, Li+ or cyclohexylammonium or Cl−, Br−, acetate, trifluoroacetate, propionate, lactate, oxalate, malonate, maleinate, citrate, benzoate, salicylate etc. Suitable solid or liquid galenic forms of preparation are instance granulates, powders, dragees, tablets, (micro) capsules, suppositories, syrups, juices, suspensions, emulsions, drops or injectable solutions (IV, IP, IM, SC) or fine dispersions (aerosols), forms of preparation for dry powder inhalation, transdermal systems, and preparations with protracted release of active ingredient, for the production of which usual means are used, such as carrier substances, explosives, binding, coating, swelling, sliding or lubricating agents, tasting agents, sweeteners and solution mediators. As auxiliary substances are named here magnesium carbonate, titanium dioxide, lactose, mannite and other sugars, talcum, milk protein, gelatin, starch, cellulose and derivatives, animal and vegetable oils such as cod-liver oil, sunflower, peanut or sesame oil, polyethylene glycols and solvents, such as sterile water and mono or multi-valent alcohols, for instance glycerin. A pharmaceutical composition according to the invention can be produced by that at least one combination of substances used according to the invention is mixed in a defined dose with a pharmaceutically suitable and physiologically well tolerated carrier and possibly further suitable active, additional or auxiliary substances, and is prepared in the desired form of administration. Preferred are solutions for injection in the usual preparation.

As dilution agents, polyglycols, ethanol, water and buffer solutions can be used. Suitable buffer solutions are for instance N,N'-dibenzylethylendiamine, diethanolamine, ethylendiamine, N-methylglucamine, N-benzylphenethylamine, diethylamine, phosphate, sodium bicarbonate, or sodium carbonate. It is however also possible not to use any dilution agent at all.

Physiologically tolerated salts, whether of the lipopeptide, or of the cyclodextrins or cyclodextrin derivatives, are salts with inorganic or organic acids, such as hydrochloric acid, sulfuric acid, acetic acid, citric acid, p-toluolsulfonic acid, or with inorganic or organic bases, such as NaOH, KOH, $Mg(OH)_2$, diethanolamine, ethylendiamine, or with amino acids, such as arginine, lysine, glutamine acid etc. or with inorganic salts, such as $CaCl_2$, NaCl or the free ions thereof, such as $Ca^{2+}$, $Na^+$, $Cl^-$, $SO_4^{2-}$ or combinations thereof. They are also produced by using standard methods.

In detail, a pharmaceutical composition according to the invention may comprise: A) 0.01 to 80 wt. %, in particular 0.05 to 50 wt. %, preferably 0.1 to 30 wt. % lipopeptide, B) 0.01 to 99 wt. %, in particular 0.05 to 80 wt. %, preferably 0.1 to 50 wt. % cyclodextrin or cyclodextrin derivative, C) 0.1 to 99.8 wt. %, in particular 1 to 80 wt. %, preferably 1 to 50 wt. % additional and/or auxiliary substances and optionally dilution agents, wherein the components A) to C) also add up to 100% and wherein the lipopeptide in a physiologically effective dose is mixed with the cyclodextrin or cyclodextrin derivative in a molar ratio lipopeptide/cyclodextrin from 1:500 to 10:1, preferably 1:100 to 10:1, most preferably 1:100 to 2:1, optionally under addition of additional and/or auxiliary substances in galenically usual additions.

As far as above and below statements are made with regard to wt. %, molar ratios and/or doses, they always refer to the so-called free acid of the lipopeptide, provided it is used in a salt form. Counter ions of salt forms are not taken into account, but are substituted by the atomic weight of hydrogen. Counter ions are rather used as additional or auxiliary substances.

The invention relates further to the use of a pharmaceutical composition according to the invention for the production of a drug for the treatment and/or prophylaxis of viral, bacterial and/or parasitary infectious diseases and/or of fungal diseases. Examples of such diseases or applications are: infections of the respiratory tract, infections of the skin and the soft parts, infections of the urinary tract, infections of the gallbladder tract, sepsis, endocarditis, meningitis, op prophylaxis, wound infections or intraabdominal infections.

It is preferred that the drug is galenically prepared for the oral administration or for the injection.

The invention furthermore relates to a method for the treatment of a bacterial, viral or parasitary infectious disease or a fungal disease, wherein a person, which has fallen ill with the disease or is in danger of falling ill therewith, is administered a physiologically effective dose of a drug according to the invention. The daily dose may be from 1 to 50,000 mg, preferably 50 to 30,000 mg, most preferably from 100 to 20,000 mg lipopeptide over a period from 1 to 60 days, preferably 1 to 30 days.

Packing units with a multitude of administration units may be provided, wherein every administration unit is prepared for an administration within the above treatment plan. For example, a packing unit may contain $n1=5$ to $n2=500$ administration units, wherein every administration unit contains $m1=\frac{1}{5}$ to $m2=1$ daily dose of lipopeptide. The packing unit is then prepared for a treatment plan, which provides 1 to 5 administrations per day over a period of o1 to o2 days, wherein o is then calculated by $o1=n1*m2$ and $o2=n2*m1$, or o and m are given and n is calculated as $n=o/m$.

In the following, the invention is explained in more detail by comparative examples and not limiting examples according to the invention.

EXAMPLE 1

Minimization of the Friulimicin B-Induced Hemolysis by Human Serum Albumin (HSA); Comparative Example $Na_2$ friulimicin B was dissolved in a concentration of 6,400 mg/l in 0.9% NaCl solution with 20, 15, 10, 5, 1 or 0% HSA. By dilution with 0.9% NaCl and the respective HSA concentrations, further stock solutions of 3,200, 1,600, 800, 200 and 100 mg/l $Na_2$ friulimicin were prepared for every one of the listed HSA concentrations. After pre-incubation for 2 hours at ambient temperature, 40 µl of the friulimicin B/HSA mixture were mixed with 40 µl of fresh venal human blood and then incubated at 37° C. for 180 min. As a negative control, mixtures of full blood were prepared with the different HSA concentrations in 0.9% NaCl, as a standard for the complete hydrolysis a mixture von 40 µl of fresh venal human blood were prepared with 40 µl water. Subsequently, the degree of the hemolysis induced by the incubation was determined as follows: The samples were cautiously mixed either with water (standard) or with 1 ml 0.9% NaCl. After centrifugation of the samples at 2,500 RFC (5 min), the absorption of the supernatant was determined in the spectral photometer at 540 nm. Before the measurement of the samples, the spectral photometer was calibrated with the respective negative control described above. For the determination of the degree of hemolysis of the different reaction batches, the measured value of the standard with complete hemolysis was set to 100%. The measured values of the different reaction batches were related to the value of this standard and given in percent. Table 1 shows the result of the hemolysis test with $Na_2$ friulimicin B and different HSA concentrations performed with human blood. The statements of the concentration of the HSA (in % wt./vol.) and of the $Na_2$ friulimicin B (in mg/l, free acid) refer to the final concentrations in the reaction batch.

TABLE 1

Hemolytic activity as a function of the Na$_2$ friulimicin B concentration (mg/l) in presence of different HSA concentrations in vitro (in %)

| | Friulimicin concentration in mg/l | | | | | |
|---|---|---|---|---|---|---|
| | 0 | 100 | 200 | 800 | 1600 | 3200 |
| Batch with 0% HSA | 0 | 4.6 | 5.2 | 6.5 | 11.8 | 13.6 |
| Batch with 2.5% HSA | 0 | 0.7 | 2 | 2.7 | 3.2 | 3.9 |
| Batch with 5% HSA | 0 | 0.1 | 1 | 1.9 | 1.7 | 1.7 |
| Batch with 7.5% HSA | 0 | 0 | 0.4 | 1.6 | 1.5 | 1.3 |
| Batch with 10% HSA | 0 | 0 | 0.3 | 0.5 | 0.8 | 0.3 |

HSA suppresses with a good efficiency the hemolysis induced by Na$_2$ friulimicin B beginning from a concentration of approx. 2.5%. The following determination of the content of free hemoglobin in the serum showed that after pre-incubation with 5%-10% HSA (wt./vol., final concentration in the reaction batch) the friulimicin B-induced hemolysis could significantly be minimized.

The determination of the antibiotic activity of such Na$_2$ friulimicin B/HSA compositions in vitro with *Staphylococcus aureus* and *Enterococcus faecalis*, measured according to the following examples according to the invention, showed however, as illustrated in Table 2, also a strong reduction of the antibiotic activity.

TABLE 2

Determination of the minimum inhibitory concentration (MIC) of Na$_2$ friulimicin in presence of HSA

| | Medium addition | MIC value [µg/ml] |
|---|---|---|
| *S. aureus* ATCC 29213 | 0% HSA | 2 |
| *S. aureus* ATCC 29213 | 4% HSA | 8 |
| *E. faecalis* ATCC 29212 | 0% HSA | 4 |
| *E. faecalis* ATCC 29212 | 4% HSA | >64 |

EXAMPLE 2

Minimization of the Hemolysis Induced by Na$_2$ by the Addition of Cyclodextrins This example shows the effect of different modified or unmodified cyclodextrins on the hemolytic effect induced by lipopeptides. Herein, Na$_2$ friulimicin B serves as an example molecule for the antibiotics of the lipopeptides.

Na$_2$ friulimicin B was dissolved in a concentration of 3,200 mg/l in 0.9% NaCl solution. By dilution with 0.9% NaCl, further stock solutions of 1,600, 800, 200, 100 and 50 mg/l Na$_2$ friulimicin were produced. 20 µl each of these stock solutions were carefully mixed with 20 µl 0.9% NaCl or 2% solutions of (2-Hydroxypropyl)-γ-cyclodextrin (HP-γ-CD), (2-Hydroxypropyl)-β-cyclodextrin (HP-β-CD) or α-cyclodextrin (α-CD) in 0.9% NaCl. The pre-incubation and test execution for the determination of the hemolytic activity with fresh venal human blood was made according to Example 1. Experiments at a final concentration of 0.5% (wt./vol.) of the different cyclodextrins and the stated final concentrations of the Na$_2$ friulimicin B (in mg/l, free acid) provided the results shown in Table 3.

TABLE 3

Hemolytic activity as a function of the Na$_2$ friulimicin concentration in presence of different cyclodextrins in vitro (in %)

| | Friulimicin concentration in mg/l | | | | | |
|---|---|---|---|---|---|---|
| Cyclodextrin conc. | 0 | 50 | 100 | 200 | 800 | 1600 |
| without cyclodextrin addition | 0 | 2.3 | 5.1 | 5.9 | 8.3 | 9.4 |
| 0.5% (wt./vol.) α-CD | 0 | 0 | 0 | 0.1 | 0.4 | 1.2 |
| 0.5% (wt./vol.) HP-β-CD | 0 | 0 | 0.3 | 0.6 | 4.4 | 5.3 |
| 0.5% (wt./vol.) HP-γ-CD | 0 | 2 | 4.8 | 5.8 | 6.6 | 8.6 |

The determination of the content of free hemoglobin in the serum showed that after pre-incubation with 0.5% HP-γ-CD, there could not be found any significant reduction of the hemolysis induced by Na$_2$ friulimicin B. γ-cyclodextrins have, due to their sugar structure, a larger volume in their hydrophobic inner pocket, compared to α and β-cyclodextrins. Surprisingly, however, after the pre-incubation with 0.5% HP-β-CD and α-CD a significant reduction of the hemolysis induced by di-sodium friulimicin B could be detected.

EXAMPLE 3

Minimization of the Ca$_2$Cl$_2$ Friulimicin B-Induced Hemolysis by the Addition of Modified β-Cyclodextrins This example shows the effect of β-cyclodextrins on the hemolytic effect induced by lipopeptides in presence of high concentrations of the lipopeptide. Herein, Ca$_2$Cl$_2$ friulimicin B serves as an example molecule for the antibiotics of the class of the lipopeptides and sulfobutylether-β-cyclodextrin (SBE-β-CD) as well as HP-β-CD as examples for modified β-cyclodextrins.

Ca$_2$Cl$_2$ friulimicin B was dissolved in a concentration of 100, 50, 40, 30, 20, 10 and 5 g/l in 20, 15, 12.5, 10, 7.5% SBE-β-CD in 0.9% NaCl solution or 12.5% HP-β-CD in 0.9% NaCl solution, respectively. The pre-incubation and test execution for the determination of the hemolytic activity with fresh venal human blood were made according to Example 1. Different therefrom, the incubation of the final reaction batches was performed with blood for 60 min at 37° C. The results are shown in Table 4. Statements of the Ca$_2$Cl$_2$ friulimicin B (in mg/l, free acid) and of the cyclodextrins refer to the final concentrations in the reaction batch.

TABLE 4

Hemolytic activity as a function of the Ca$_2$Cl$_2$ friulimicin concentration in presence of different cyclodextrins in vitro (in %)

| | Friulimicin concentration in g/l | | | | | |
|---|---|---|---|---|---|---|
| Cyclodextrin conc. | 0 | 5 | 10 | 15 | 20 | 25 |
| without cyclodextrin addition | 0 | 76 | 87 | 91 | 93 | 97 |
| 7.5% (wt./vol.) SBE-β-CD | 0 | 0 | 1 | 3 | 18 | 63 |
| 10% (wt./vol.) SBE-β-CD | 0 | 0 | 1 | 3 | 13 | 42 |
| 12.5% (wt./vol.) SBE-β-CD | 0 | 0 | 0 | 1 | 4 | 12 |
| 15% (wt./vol.) SBE-β-CD | 0 | 0 | 0 | 1 | 1 | 4 |

Surprisingly, it could be found that HP-β-CD, in particular however also SBE-β-CD itself suppress at very high concentrations of the hemolytically very active Ca$_2$Cl$_2$ salt of friulimicin B the hemolysis induced by the active agent. These results show that even with extreme active agent concentrations, which occur for a short time only immediately at injection or infusion positions, the hemolytic effect of $Ca_2Cl_2$ friulimicin B can significantly be suppressed after pre-incubation with modified β-cyclodextrins over a period of one hour.

EXAMPLE 4

Minimization of the Daptomycin-Induced Hemolysis by the Addition of Modified β-Cyclodextrins This example shows the effect of a sulfoalkylether cyclodextrin on the hemolytic effect induced by the lipopeptide daptomycin with isolated erythrocytes in the presence of $CaCl_2$.

Daptomycin was dissolved in a solution of 0% or 2.5% SBE-β-CD in 0.9% NaCl, 2.5 mM $CaCl_2$. For performing the hemolysis tests, erythrocytes from fresh venal human blood, which was collected in heparinized sample tubes, were isolated. For this purpose, the erythrocytes were sedimented by centrifugation at 2,500 RFC (5 min). The erythrocytes were washed three times with 0.9% NaCl and after the final centrifugation received in a volume of 0.9% NaCl, which corresponded to the initial volume of the blood sample. 40 μl of the erythrocytes were reacted with 40 μl of the above reaction batches and incubated for 5 hours at 37° C. under continuous careful shaking. The further execution of the test for the determination of the hemolytic activity was made according to Example 1. The results are shown in Table 5. Statements of the concentrations of SBE-β-CD (in % wt./vol.) and of the daptomycin (in mg/l, free acid) refer to the final concentrations in the reaction batch.

TABLE 5

Hemolytic activity as a function of the daptomycin concentration in presence of SBE-β-CD in vitro (in %)

| | Daptomycin conc. in (mg/l) | | | | |
| --- | --- | --- | --- | --- | --- |
| Cyclodextrin conc. | 0 | 1,600 | 3,200 | 6,400 | 12,800 |
| 0% | 0 | 1.7 | 6.5 | 7.6 | 7.8 |
| 1.25% (wt./vol.) SBE-β-CD | 0 | 0 | 0.1 | 0.1 | 0 |

SBE-β-CD suppressed also in the experiment with isolated erythrocytes the cell lysis induced by a lipopeptide, here daptomycin. This experiment shows that SBE-β-CD can suppress toxic properties of very different lipopeptides. The hemolytic properties of the daptomycin are based on an immediate interaction with the erythrocyte membrane. Similar mechanisms cause the toxic effect described for daptomycin on the skeletal muscle, so that a formulation of daptomycin or its derivatives with cyclodextrins minimizes this toxic effect, too.

EXAMPLE 5

Effects of the Additions of Cyclodextrins on the Antibiotic Activity of $Ca_2Cl_2$ Friulimicin B The effects of cyclodextrins on the antibiotic activity von $Ca_2Cl_2$ friulimicin B were investigated by in vitro experiments about the growth inhibition of Gram-positive bacteria. Herein, the minimum inhibitory concentration for the growth inhibition was determined by cultivation of the bacteria on nutritious agar (agar dilution) according to the CLSI (previously NCCLS) rules (National Committee for Clinical Laboratory Standards. 2003. Methods for dilution antimicrobial susceptibility tests for bacteria that grow aerobically; approved standard—6th ed. Document M7-A6. Clinical and Laboratory Standards Institute, Wayne, Pa., USA). Different molar mixture ratios of the lipopeptide $Ca_2Cl_2$ friulimicin B were tested with SBE-β-CD in Ca ions-adjusted Müller-Hinton medium. The Gram-positive strains tested for the cultivation methods were:

*Staphylococcus carnosus* ATCC 51365 {DSM 20501)
*Staphylococcus aureus* ATCC 29213 (DSM 2569)
*Staphylococcus aureus* ATCC 33592 (DSM 11729)
*Staphylococcus epidermidis* ATCC 12228 (DSM 1798)

The employed quantities of cells per spot (intended value: $5*10^3-5*10^4$ CFU) were:
*S. carnosus* ATCC 51365 $5.5*10^3$ CFU
*S. aureus* ATCC 29213 $7.6*10^3$ CFU
*S. aureus* ATCC 33592 $2.2*10^4$ CFU
*S. epidermidis* ATCC 12228 $1.1*10^4$ CFU

TABLE 6

Antibiotic activity (MIC in μg/ml) of $Ca_2Cl_2$ friulimicin B as a function of the SBE-β-CD quantity (given is the molar ratio of the quantities) in vitro

| | Friulimicin:SBE-β-CD | | |
| --- | --- | --- | --- |
| | 1:0 | 1:2.5 | 1:4 |
| *S. carnosus* ATCC51365 | 0.5 | 0.5 | 0.5 |
| *S. aureus* ATCC29213 | 0.5 | 0.5 | 0.5 |
| *S. aureus* ATCC33592 | 1 | 1 | 1 |
| *S. epidermidis* ATCC12228 | 0.5 | 0.5 | 0.5 |

Surprisingly, the cyclodextrin does not negatively affect in these experiments the antibiotic activity of $Ca_2Cl_2$ friulimicin B, although by the molecular interaction of the cyclodextrins with friulimicin at the same molar ratios the hemolytic property of the lipopeptide can nearly completely be suppressed.

EXAMPLE 6

Inhibition of the Hemolytic Activity of Different Lipopeptides by Cyclodextrins

This example shows the effect of a sulfoalkylether cyclodextrin on the hemolytic effect induced by different lipopeptides. The lipopeptides were dissolved in a concentration von 6,400 mg/l in 0.9% NaCl solution. By dilution with a volume 0.9% NaCl or 0.9% NaCl/10% SBE-β-CD were respectively produced stock solutions of 3,200 mg/l lipopeptide (free acid) with or without 5% SBE-β-CD. The pre-incubation and the execution of the test for the determination of the hemolytic activity with fresh venal human blood were made according to Example 1 and supplied the results shown in Table 7. There is shown the percentage inhibition of the lipopeptide-induced hemolysis by the presence von 2.5% SBE-β-CD at a lipopeptide concentration of 1,600 mg/l. The tested lipopeptides are friulimicin derivatives and amphomycin derivatives, the acyl residue of which was modified. All lipopeptides have a structure according to formula I

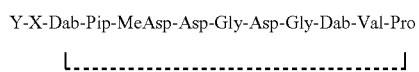
formula I wherein the investigated lipopeptides are characterized as follows:

|  | X | Y |
|---|---|---|
| Amphomycin | Asp | 10-methyldodec-3-ene acid |
| Friulimicin B | Asn | 12-methyltridec-3-ene acid |
| CBS000201 | Asn | 12-methyltridecanoic acid |
| CBS000205 | Asn | 15-phenyl-n-pentadecancarbonic acid |
| CBS000203 | Asn | stearic acid |
| CBS000204 | Asn | γ-linolenic acid |
| CBS000217 | Asn | 4-[2-(4-Phenethyl-phenyl)-ethyl]-benzoic acid | and Y was linked by amidation with the extra circular Asn or Asp of the peptide. In detail, for the production of such lipopeptides is for instance made reference to the document EP 0 688 789 A1.

TABLE 7

Inhibition of the hemolytic activity of different lipopeptides at a concentration of 1,600 mg/l in presence of 2.5% SBE-β-CD

| Lipopeptide | Reduction of the hemolysis in % |
|---|---|
| Amphomycin | 99.6% |
| $Ca_2Cl_2$ friulimicin B | 99.2% |
| CBS000201 | 95.7% |
| CBS000205 | 74.9% |
| CBS000203 | 41.3% |
| CBS000204 | 87.0% |
| CBS000217 | 99.5% |

These results show that cyclodextrins are substantially independently from the acyl and peptidyl residue of lipopeptides capable to reduce the hemolysis.

EXAMPLE 7

Production of a $Ca_2Cl_2$ Friulimicin B Injection Solution 100 mg $Ca_2Cl_2$ friulimicin B and 770 mg SBE-β-CD are dissolved in a sterile 0.9% NaCl solution, filtrated through a polyethersulfone membrane (0.2 μm, non-pyrogenic) and lyophilized. The whole lyophilisate is then dissolved in 10 ml water for injection solutions, filled into a sterile ampule. Then the ampule is sealed with a septum.

EXAMPLE 8

Minimization of the Hemolysis Induced by $Ca_2Cl_2$ Friulimicin B by the Addition of Different Concentrations of Sulfobutylether-β-Cyclodextrin (SBE-β-CD)

This example shows the effect of different ratios of cyclodextrins to lipopeptides on the hemolytic effect induced by the lipopeptides. Herein, $Ca_2Cl_2$ friulimicin B serves as an example molecule for the antibiotics of the class of the lipopeptides and sulfobutylether-β-cyclodextrin (SBE-β-CD) as an example molecule for the cyclodextrins.

$Ca_2Cl_2$ friulimicin B was dissolved in a concentration of 2,500 mg/l in 0.9% NaCl solution. To different batches of this 0.9% NaCl solution were added different SBE-β-CD concentrations, so that the following molar ratios (SBE-β-CD:friulimicin B) were generated: 0:1; 1:10; 1:5; 1:1; 2.5:1; 5:1; 10:1.

The pre-incubation and the execution of the test for the determination of the hemolytic activity with fresh venal human blood were made according to Example 1. In Table 8 is shown, which share of the hemolysis induced by 2,500 mg/l $Ca_2Cl_2$ friulimicin B in absence of SBE-β-CD is reduced by the addition of SBE-β-CD in the mentioned molar ratios.

Statements of the content of $Ca_2Cl_2$ friulimicin B (in mg/l) refer to the final concentrations of the free acid of the friulimicin B in the reaction batch. The statements of the molar ratios respectively refer to the free acids of friulimicin B and SBE-β-CD.

TABLE 8

Reduction of the hemolysis induced by 2,500 mg/l $Ca_2Cl_2$ friulimicin B by SBE-β-CD in vitro (in %)

| Molar ratio SBE-β-CD:friulimicin B | Reduction of the induced hemolysis |
|---|---|
| 0:1 | 0% |
| 1:10 | 11% |
| 1:5 | 28% |
| 1:1 | 80% |
| 2.5:1 | 96% |
| 5:1 | 98% |
| 10:1 | 100% |

Surprisingly it could be found that SBE-β-CD suppressed already in substoechiometric concentrations the hemolysis induced by $Ca_2Cl_2$ friulimicin B even at a friulimicin B concentration of 2,500 mg/l during an incubation duration of 3 hours.

EXAMPLE 9

Effect of Cyclodextrins on the Hemolytic Activity of a Cyclic Peptide

This example concerns the inhibition of the hemolytic activity of different lipopeptides by cyclodextrins and shows the effect of a sulfoalkylether cyclodextrin on the hemolytic effect induced by the cyclic peptide tyrocidin. Tyrocidin was dissolved in a concentration of 6,400 mg/l in 0.9% NaCl solution. By dilution with a volume of 0.9% NaCl or 0.9% NaCl/10% SBE-β-CD, stock solutions of 3,200 mg/l tyrocidin with or without 5% SBE-β-CD, respectively, were prepared. The pre-incubation the execution of the test for the determination of the hemolytic activity with fresh venal human blood were made according to Example 1. The evaluation of this experiment showed that the hemolysis induced by 1,600 mg/l tyrocidin in presence of 2.5% SBE-β-CD is increased by 178%. The addition of cyclodextrins thus does not suppress for every hemolytically acting substance the lysis of the erythrocytes.

EXAMPLE 10

Minimization of the Hemolysis Induced by $Ca_2Cl_2$ Friulimicin B with Canine Blood by Sulfobutylether-β-Cyclodextrin (SBE-β-CD)

This example shows the effect of β-cyclodextrins on the lipopeptide-induced hemolytic effect with blood of different organisms. Herein, $Ca_2Cl_2$ friulimicin B serves as an example molecule for the antibiotics of the class of the lipopeptides and sulfobutylether-β-cyclodextrin (SBE-β-CD) as examples for modified β-cyclodextrins. The experiments were made with canine blood.

$Ca_2Cl_2$ friulimicin B was dissolved in 0.9% NaCl solution with and without addition of SBE-β-CD. In the batch with SBE-β-CD there was a molar ratio (SBE-β-CD:friulimicin B) of 2.5:1. The pre-incubation and the execution of the test for the determination of the hemolytic activity with venal canine blood were made according to Example 1. The results are shown in Table 9. Statements of the content of $Ca_2Cl_2$ friulimicin B (in mg/l) refer to the final concentrations of the free acid of the friulimicin B in the reaction batch. The statements of the molar ratio refer to the free acids of friulimicin B and SBE-β-CD, respectively.

TABLE 9

Reduction of the hemolysis induced by $Ca_2Cl_2$ friulimicin B by SBE-β-CD in vitro with canine blood (in %)

| Friulimicin B concentration | Reduction of the hemolysis by the addition of SBE-β-CD |
|---|---|
| 800 | 55% |
| 5,000 | 100% |

The example shows that SBE-β-CD in a molar ratio of 2.5:1 (SBE-β-CD:friulimicin B) suppresses the lysis induced by $Ca_2Cl_2$ friulimicin B of erythrocytes in canine blood.

EXAMPLE 11

Minimization of the Hemolysis Induced by $Ca_2Cl_2$ Friulimicin B with Blood of Macaques (Macaca Fascicularis) by Sulfobutylether-β-Cyclodextrin (SBE-β-CD)

This example shows the effect of β-cyclodextrins on the hemolytic effect induced by lipopeptides with the blood of different organisms. Herein, $Ca_2Cl_2$ friulimicin B serves as an example molecule for the antibiotics of the class of the lipopeptides and sulfobutylether-β-cyclodextrin (SBE-β-CD) as an example for cyclodextrins. The experiments were made with the blood of macaques.

$Ca_2Cl_2$ friulimicin B was dissolved in 0.9% NaCl solution with and without addition of SBE-β-CD. In the batch with SBE-β-CD, there was a molar ratio (SBE-β-CD:friulimicin B) of 5:1. The pre-incubation and the execution of the test for the determination of the hemolytic activity with venal macaque blood were made according to Example 1. Statements of the content of $Ca_2Cl_2$ friulimicin B (in mg/l) refer to the final concentrations of the free acid of the friulimicin B in the reaction batch. The statements of the molar ratio refer to the free acids of friulimicin B and SBE-β-CD, respectively.

TABLE 10

Reduction of the hemolysis induced by $Ca_2Cl_2$ friulimicin B by SBE-β-CD in vitro with blood of macaques (in %)

| Friulimicin B concentration | Reduction of the hemolysis by the addition of SBE-β-CD |
|---|---|
| 3,200 | 92% |
| 6,400 | 99% |

The example shows that SBE-β-CD in a molar ratio of 5:1 (SBE-β-CD:friulimicin B) suppresses the lysis induced by $Ca_2Cl_2$ friulimicin B of erythrocytes in the blood of macaques.

EXAMPLE 12

Influence of the Antibiotic Activity of Lipopeptides by Cyclodextrins In Vivo

This example shows the effect of β-cyclodextrins on the antibiotic activity of lipopeptides in vivo. Herein, $Ca_2Cl_2$ friulimicin B serves as an example molecule for the antibiotics of the class of the lipopeptides and sulfobutylether-β-cyclodextrin (SBE-β-CD) as examples for modified β-cyclodextrins. Shown are the results of a study with an intranasal lung infection model in the mouse.

$Ca_2Cl_2$ friulimicin B was dissolved in 0.9% NaCl solution with and without addition of SBE-β-CD. In the batch with SBE-β-CD, there was a molar ratio (SBE-β-CD:friulimicin B) of 2.5:1. The statements of the $Ca_2Cl_2$ friulimicin B concentration (in mg/l) refer to the final concentrations of the free acid of the friulimicin B in the reaction batch. The statements of the molar ratios refer to the free acids of friulimicin B and SBE-β-CD, respectively.

Female mice (CFW-1 (Harlan Winkelmann, Germany)) were infected intranasally with *Streptococcus pneumoniae* L3TV ($1*10^6$ CFU/mouse). 1 and 4 hours after the infection, the animals were subcutaneously administered a total dose of 20 mg $Ca_2Cl_2$ friulimicin B/kg with and without SBE-BCD (5%). 24-hours after the infection, a determination of the number of germs in the lung was performed by plating-out of a tissue disintegration on agar plates in a manner the man skilled in the art is familiar with. The evaluation of this study showed that surprisingly SBE-β-CD increases the antibiotic effect of $Ca_2Cl_2$ friulimicin B (Mann Whitney Test p=0.0159).

EXAMPLE 13

Influence of the Acute Toxicity of Lipopeptides by Cyclodextrins In Vivo

This example shows the effect of β-cyclodextrins on the acute toxic effects in mice caused by high concentrations of lipopeptides. Herein, $Ca_2Cl_2$ friulimicin B serves as an example molecule for the antibiotics of the class of the lipopeptides and sulfobutylether-β-cyclodextrin (SBE-β-CD) as examples for modified β-cyclodextrins.

$Ca_2Cl_2$ friulimicin B was dissolved in 0.9% NaCl solution with and without addition of SBE-β-CD. In the batch with SBE-β-CD, there was a molar ratio (SBE-β-CD:friulimicin B) of 2.5:1. The statements of the $Ca_2Cl_2$ friulimicin B concentration (in mg/l) refer to the final concentrations of the free acid of the friulimicin B in the reaction batch. The statements of the molar ratio refer to the free acids of friulimicin B and SBE-β-CD, respectively.

Female mice (CFW-1 (Harlan Winkelmann, Germany)) were administered once (iv) the $Ca_2Cl_2$ friulimicin B solutions with and without SBE-β-CD. The mortality rate of the animals within 24 hours was determined. It is shown in Table 11.

TABLE 11

Mortality rate of mice after one-time iv administration of $Ca_2Cl_2$ friulimicin B with and without SBE-β-CD (in %).

| Friulimicin B with addition of SBE-β-CD | Friulimicin B without addition of SBE-β-CD | Mortality rate within 24 hours |
|---|---|---|
|  | 300 mg/kg | 0% (0/3) |
|  | 350 mg/kg | 66% (2/3) |
|  | 400 mg/kg | 100% (3/3) |
| 300 mg/kg |  | 0% (0/3) |
| 400 mg/kg |  | 0% (0/3) |

The example shows that the acute toxicity of $Ca_2Cl_2$ friulimicin B by the presence of SBE-β-CD in a molar ratio of 2.5:1 (SBE-β-CD friulimicin B) is reduced.

The invention claimed is:

1. A pharmaceutical composition comprising an active agent comprising a lipopeptide or a derivative thereof and an α-cyclodextrin or derivative thereof or a β-cyclodextrin or derivative thereof, wherein the lipopeptide or derivative thereof has a structure according to formula I formula I Y-X-Dab-Pip-MeAsp-Asp-Gly-Asp-Gly-Dab-Val-Pro
  └─────────────────────────────────────┘ wherein X=one of the amino acids Asn or Asp, wherein Y is selected from the group consisting of:
$(CH_3)_2CH(CH_2)_7CH=CHCH_2CO-$, $CH_3(CH_2)_6CO-$, $CH_3(CH_2)_7CO-$, $CH_3(CH_2)_8CO-$, $CH_3(CH_2)_9CO-$, $(CH_3(CH_2)_{10}CO-$, $CH_3(CH_2)_{11}CO-$, $CH_3(CH_2)_{12}CO-$, $CH_3(CH_2)_{13}CO-$, $CH_3(CH_2)_{14}CO-$, $CH_3(CH_2)_{15}CO-$, $CH_3(CH(CH_3)(CH_2)_8CO-$, $CH_3CH(CH_3)(CH_2)_9CO-$, $CH_3CH(CH_3)(CH_2)_{10}CO-$, $CH_3CH(CH_3)(CH_2)_{11}CO-$, $CH_3CH(CH_3)(CH_2)_{12}CO-$, $H_2C=CH(CH_2)_8CO-$, $H_2C=CH(CH_2)_9CO-$, $CH_3(CH_2)_7CH=CHCO-$ (trans), $CH_3(CH_2)_8CH=CHCO-$ (trans), $CH_3(CH_2)_{12}CH=CHCO-$ (trans), $CH_3(CH_2)_3CH=CH(CH_2)_7CO-$ (cis), $CH_3(CH_2)_3CH=CH(CH_2)_7CO-$ (trans), $CH_3(CH_2)_3CH=CH(CH_2)_8CO-$ (trans), $CH_3(CH_2)_5CH=CH(CH_2)_7CO-$ (cis), $CH_3(CH_2)_5CH=CH(CH_2)_7CO-$ (trans), $CH_3(CH_2)_5CH=CH(CH_2)_8CO-$ (cis), $CH_3(CH_2)_{10}CH=CH(CH_2)_4CO-$ (cis), $CH_3(CH_2)_{10}CH=CH(CH_2)_4CO-$ (trans), $CH_3(CH_2)_7CH=CH(CH_2)_7CO-$ (cis), $CH_3(CH_2)_7CH=CH(CH_2)_7CO-$ (trans), $CH_3(CH_2)_5CH=CH(CH_2)_9CO-$ (trans), $CH_3(CH_2)_3(CH_2CH=CH)_2(CH_2)_7CO-$ (cis), $CH_3(CH_2)_3(CH_2CH=CH)_2(CH_2)_2CO-$ (trans), $CH_3(CH_2)_3(CH_2CH=CH)_2(CH_2)_9CO-$ (cis), $CH_3(CH_2CH=CH)_3(CH_2)_7CO-$ (cis), $CH_3(CH_2)_3(CH_2CH=CH)_3(CH_2)_4CO-$ (cis), $CH_3(CH_2CH=CH)_4(CH_2)_4CO-$ (cis), $CH_3(CH_2)_3(CH_2CH=CH)_4(CH_2)_3CO-$ (cis), $CH_3(CH_2CH=CH)_6(CH_2)_2CO-$ (cis), $H_2C=CH(CH_3)_8CO-$, $CH_3(CH_2)_3CH=CH(CH_2)_7CO-$, $CH_3(CH_2)_7CH=CH(CH_2)_7CO-$, $CH_3(CH_2)_4CH=CH-CH=CH-$ $(CH_2)_8CO-$, $(CH_3)_2C=CHCH_2[CH_2C(CH_3)=CHCH_2]_2CO-$, $Phe-Phe-CH_2CO-$, $Phe-(CH_2)_9CO-$, $Phe-O-(CH_2)_{10}CO-$, $CH_3(CH_2)_7-Phe-CO-$, $Phe-Phe-CO-$, $CH_3(CH_2)_6-Phe-CO-$, $CH_3(CH_2)_6-O-Phe-CO$, $CH_3(CH_2)_7-O-Phe-CO-$, $Phe-(CH_2)_2-Phe-CO-$, $CH_3CH_2-Phe-(CH_2)_2-Phe-CO-$, $Phe-Phe-(CH_2)_2-Phe-CO-$, $Phe-(CH_2)_2-Phe-(CH_2)_2-Phe-CO-$, $CH_3(CH_2)_3-Phe-(CH_2)_2-Phe-CO-$, $CH_3(CH_2)_5-O-Phe-(CH_2)_2-Phe-CO-$, $(CH_3)_2CH(CH_2)_6CH=CHCH_2CO-$ (cis), $(CH_3)_2CH(CH_2)_6CH=CHCH_2CO-$ (trans), $(CH_3)_2CH(CH_2)_7CH=CHCH_2CO-$ (cis), $(CH_3)_2CH(CH_2)_7CH=CHCH_2CO-$ (trans), $CH_3CH_2(CHCH_3)(CH_2)_5CH=CHCH_2CO-$ (cis), $CH_3CH_2(CHCH_3)(CH_2)_5CH=CHCH_2CO-$ (trans), $CH_3CH_2(CHCH_3)(CH_2)_7CH=CHCH_2CO-$ (cis), $CH_3CH_2(CHCH_3)(CH_2)_7CH=CHCH_2CO-$ (trans), $CH_3CH_2(CHCH_3)(CH_2)_7CH=CHCH_2CO-$ (cis), $CH_3(CH_2)_8CH=CHCO-$ (cis), $CH_3(CH_2)_8CH=CHCO-$ (trans), $CH_3(CH_2)_9CH=CHCO-$ (cis), $CH_3(CH_2)_8CH=CHCO-$ (trans), $CH_3(CH_2)_7CH=CHCO-$ (cis), $CH_3(CH_2)_7CH=CHCO-$ (trans), wherein Phe is a benzene ring being not substituted or substituted one time or two to four times by C1-8 alkyl, and wherein -Phe- is ortho, meta, or para bonding, or a physiologically tolerated salt of such a compound.

2. The pharmaceutical composition according to claim 1, wherein the lipopeptide is selected from the group consisting of amphomycin and amphomycin derivatives.

3. The pharmaceutical composition according to claim 1, comprising several different lipopeptides, each in a physiologically effective dose.

4. The pharmaceutical composition according to claim 1, wherein the lipopeptide is present as an alkali or alkaline earth salt, comprising a Na or calcium salt further comprising a di-calcium salt ($Ca_2Cl_2$ salt) or an ammonium salt, or wherein the lipopeptide is neutral, or wherein the lipopeptide is present as a cationic part of a salt comprising a counter ion further comprising an ion selected from the group consisting of hydrochloride, sulfonate, nitrate, phosphate, succinate, maleate, citrate, tartrate, lactate, gluconate and sulfonate.

5. The pharmaceutical composition according to claim 1, comprising the lipopeptide in a total quantity from 0.001 to 20 wt. %.

6. The pharmaceutical composition according to claim 1, wherein the α- or β-cyclodextrin or derivative of said α- or β-cyclodextrin has the general formula II Formula II wherein $R_1$, $R_2$, and $R_3$ may be identical or different and residue, preferably —H, C1-C8 alkyl, —$SO_2OH$, —$PO(OH)_2$, or —CO—R4 with R4=C1-C8 alkyl, wherein the C1-C8 alkyl may be single or multiple at identical or at different C atoms with —OH, —COOH, —$CONHR_5$, —$NHCOR_6$, —$SO_2OH$, —$PO(OH)_2$, or tetrazol-5-yl with $R_5$=—H or C1-C4 alkyl and $R_6$=carboxylphenyl, wherein n=6 or 7.

7. The pharmaceutical composition according to claim 1, wherein the cyclodextrin or cyclodextrin derivative is selected from the group consisting of α-cyclodextrin, β-cyclodextrin, hydroxy-(C1-C8 alkyl)-α-cyclodextrin, hydroxy-(C1-C8 alkyl)-β-cyclodextrin, (2-hydroxypropyl)-β-cyclodextrin, (2-hydroxypropyl)-α-cyclodextrin, sulfo-(C1-C8 alkyl)-ether-α-cyclodextrin, sulfo-(C1-C8 alkyl)-ether-β-cyclodextrin, sulfobutylether-α-cyclodextrin, sulfobutylether-β-cyclodextrin.

8. The pharmaceutical composition according to claim 1, comprising the cyclodextrin or cyclodextrin derivative in a quantity from 0.001 to 50 wt. %.

9. The pharmaceutical composition according to claim 1, comprising further additional or auxiliary substances comprising galenic auxiliary substances.

10. The pharmaceutical composition according to claim 9, comprising
   a) 0.001 to 20 wt. % of the lipopeptide,
   b) 0.001 to 79.9 wt. % of the cyclodextrin or cyclodextrin derivative,
   c) 0.1 to 99.998 wt. % of the additional or auxiliary substances or dilution agents,
wherein the components a) to c) always add up to 100%.

11. The pharmaceutical composition according to claim 1, wherein said lipopeptide is selected from the group consisting of friulimicin, friulimicin B and friulimicin derivatives and a β-cyclodextrin or derivative thereof.

12. The pharmaceutical composition according to claim 1, wherein said lipopeptide is selected from the group consisting of amphomycin, amphomycin derivatives, friulimicin, friulimicin B, friulimicin derivatives and an α-cyclodextrin or derivative thereof or a physiologically tolerated salt of such a compound.

13. A pharmaceutical composition comprising friulimicin B or a physiologically tolerated salt of friulimicin B and an α-cyclodextrin or a β-cyclodextrin or derivative thereof or a physiologically tolerated salt of said α-or β-cyclodextrin or derivative thereof.

14. A pharmaceutical composition comprising friulimicin B or a physiologically tolerated salt of friulimicin B and sulfobutylether-β-cyclodextrin (SBE-β-CD).

* * * * *